(12) United States Patent
Kopp et al.

(10) Patent No.: US 7,315,017 B2
(45) Date of Patent: Jan. 1, 2008

(54) OPTICAL DEVICE PRODUCING TWO BEAMS CAPABLE OF REACHING A COMMON SENSOR

(75) Inventors: Christophe Kopp, Meylan (FR); Vincent Liot, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 86 days.

(21) Appl. No.: 10/528,358

(22) PCT Filed: Oct. 1, 2003

(86) PCT No.: PCT/FR03/02880

§ 371 (c)(1),
(2), (4) Date: May 25, 2005

(87) PCT Pub. No.: WO2004/034039

PCT Pub. Date: Apr. 22, 2004

(65) Prior Publication Data

US 2005/0200964 A1 Sep. 15, 2005

(30) Foreign Application Priority Data

Oct. 11, 2002 (FR) .................................. 02 12684

(51) Int. Cl.
*H01J 3/14* (2006.01)
*G06M 7/00* (2006.01)
*G02B 27/30* (2006.01)

(52) U.S. Cl. ....................... 250/216; 250/221; 359/641

(58) Field of Classification Search ................ 250/216, 250/221, 343, 347; 356/124, 126, 436, 437, 356/441, 442; 359/641
See application file for complete search history.

(56) References Cited

U.S. PATENT DOCUMENTS

| 4,305,659 A | | 12/1981 | Bilstad et al. ................. 356/40 |
| 4,709,146 A | * | 11/1987 | Reitsema ............... 250/231.14 |
| 4,880,304 A | | 11/1989 | Jaeb et al. .................... 356/41 |
| 5,608,220 A | * | 3/1997 | Wieser et al. ............... 250/353 |
| 5,847,819 A | * | 12/1998 | Yanagi ........................ 356/124 |
| 6,151,522 A | * | 11/2000 | Alfano et al. ................ 600/473 |

FOREIGN PATENT DOCUMENTS

| DE | 10 79 857 B | 4/1960 |
| EP | 0 457 624 A | 11/1991 |
| EP | 0 489 546 A | 6/1992 |

* cited by examiner

*Primary Examiner*—Que Tan Le
*Assistant Examiner*—Pascal M Bui-Pho
(74) *Attorney, Agent, or Firm*—Oliff & Berridge, PLC

(57) ABSTRACT

The optical device comprises a first and a second optical sources respectively emitting a first incident beam and a second light beam of different wavelength. Reflecting means, which may be a mirror, are arranged on the optical path of the first incident beam so as to form a reflected light beam. The reflecting means are arranged outside and proximate to the optical path of the second light beam so that the reflected beam and the second light beam pass through a zone of the space, wherein an object to be analyzed is to be exposed, and reach a common sensor.

9 Claims, 6 Drawing Sheets

OPTICAL DEVICE PRODUCING TWO BEAMS CAPABLE OF REACHING A COMMON SENSOR

BACKGROUND OF THE INVENTION

The invention relates to an optical device comprising reflecting means arranged on the optical path of an incident beam emitted by a first optical source so as to form a reflected light beam, and a second optical source producing a second light beam of different wavelength so that the reflected beam and the second light beam pass through a zone of the space, wherein an object to be analyzed is to be exposed, and reach a common sensor.

STATE OF THE ART

A first known device (FIG. 1), enabling two beams emitted by two optical sources to reach the same sensor, comprises two optical sources 1 and 2, arranged substantially side by side, the orientation of one of the two sources being able to be adjusted to focus the beam emitted by this source onto the sensor. The divergence of the two optical sources 1 and 2 is previously reduced by two collimating lenses 3 and 4, each enabling an angle of divergence of less than 10° to be obtained. The device using an optical source with adjustable orientation is however very cumbersome and the diversion between the two beams is often too large. Moreover, it is not always possible to balance the power emitted by each of the sources.

A second known device (FIG. 2 and U.S. Pat. No. 4,305,659) comprises two optical sources 1 and 2 arranged in such a way as to emit substantially perpendicular beams, and a separating plate 6 arranged at the intersection of the two optical beams. An absorbing element 7 can be arranged on the optical path of one of the two beams so as to attenuate the power thereof. The separating plate 6 does however cause a power loss of at least 50% on the total power of the two beams. In addition, with this type of assembly, only two optical sources can be mounted at the same time.

In the document DE 1,079,857, a mirror, also arranged at the intersection of the two beams, comprises a central orifice designed to let one of the two beams pass without diverting it. In this conformation, the presence of the central orifice causes the loss of a part of the beam reflected by the mirror, which reduces the power of the beam reflected by the mirror.

OBJECT OF THE INVENTION

The object of the invention is to provide an optical device enabling two beams to be produced focussing on a single sensor, while controlling the optical power received by the sensor.

According to the invention, this object is achieved by the accompanying claims and more particularly by the fact that the reflecting means are arranged proximate to the optical path of the second beam.

According to a development of the invention, the optical device comprises means for deforming the reflecting means.

According to a preferred embodiment of the invention, the optical device comprises means for orienting the reflecting means.

According to another feature of the invention, the optical device comprises a collimating lens common to the first and second sources and arranged at the intersection of the first incident beam and of the second beam.

BRIEF DESCRIPTION OF THE DRAWINGS

Other advantages and features will become more clearly apparent from the following description of particular embodiments of the invention given as non-restrictive examples only and represented in the accompanying drawings, in which.

DESCRIPTION OF PARTICULAR EMBODIMENTS

Figure 3:
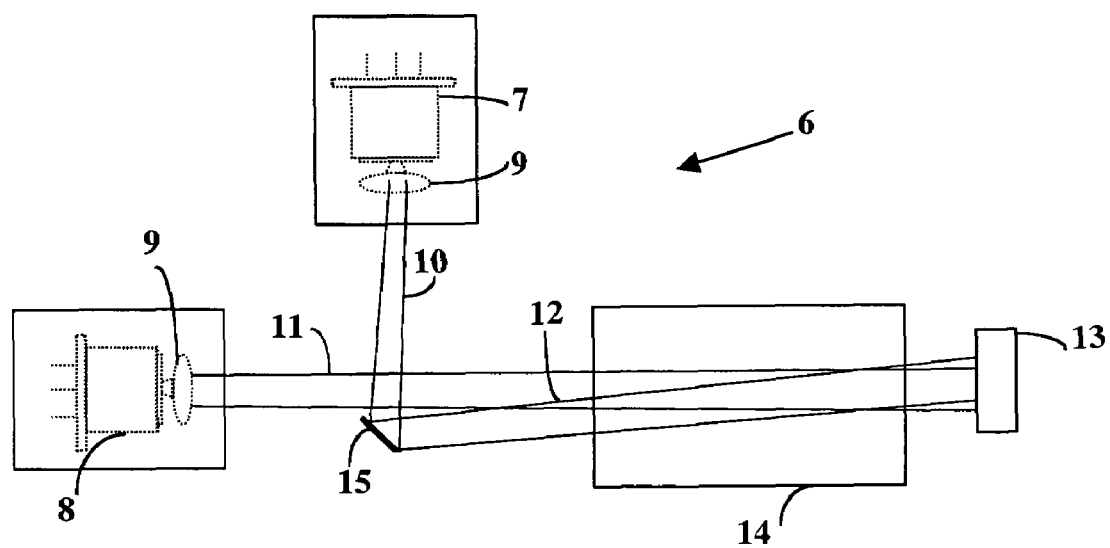
FIG. 3 is a schematic representation of a first embodiment of an optical device according to the invention.

According to a first embodiment represented in FIG. 3, an optical device 6 comprises a first optical source 7 and a second optical source 8, arranged orthogonally. The optical sources 7 and 8 can be of any type. They can be different from one another or similar, emit a coherent or incoherent light. They are for example formed by a laser diode, an incandescent lamp filament, a light-emitting diode or a laser.

In FIG. 3, the first and second optical sources 7 and 8 are divergent optical sources each comprising a collimating lens 9 designed to reduce the divergence of the beam produced by each optical source. The first and second optical sources 7 and 8 respectively emit a first incident light beam 10 and a second light beam 11 of different wavelength from that of the first incident beam 11.

Figure 1:
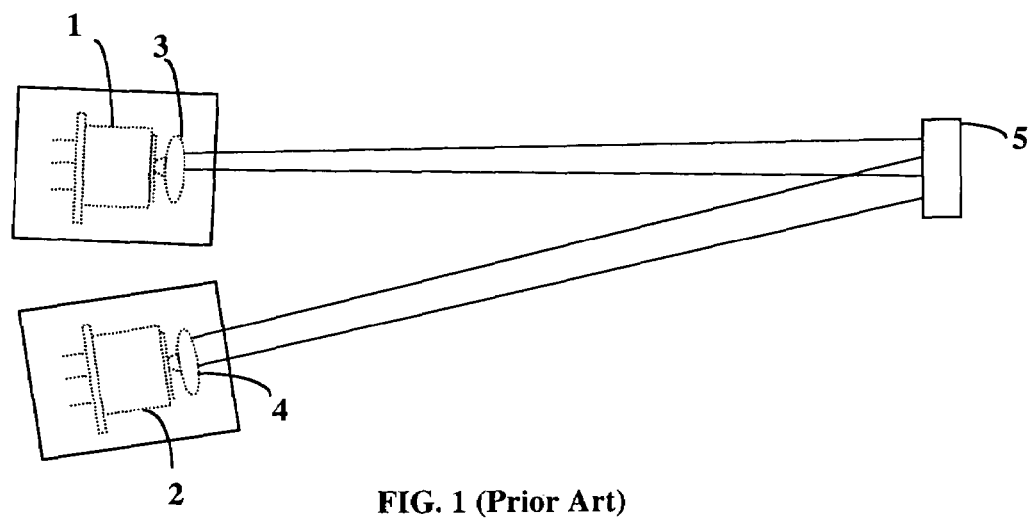
FIGS. 1 and 2 schematically represent two optical devices according to the prior art.
Figure 2:
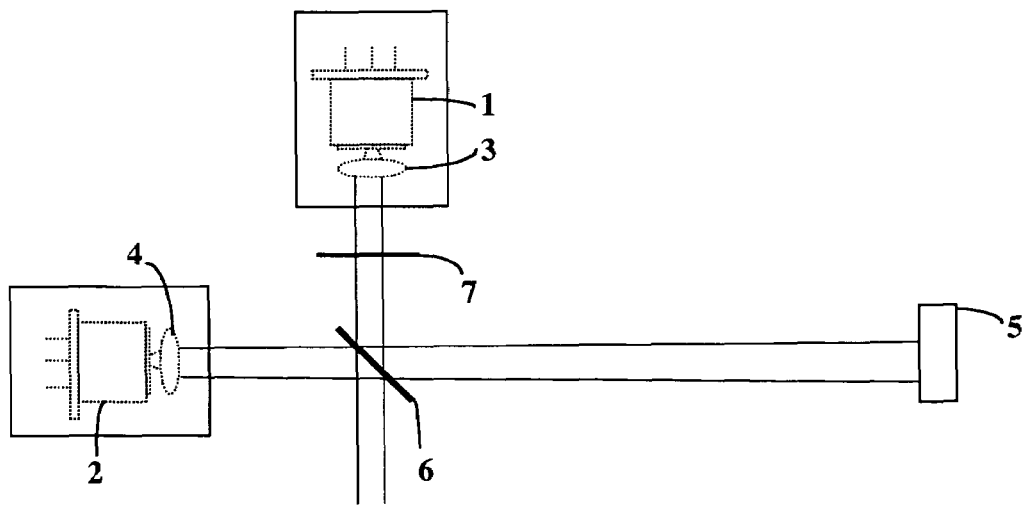

Reflecting means, formed by a mirror 15 in FIG. 3 and arranged on the optical path of the incident beam 10, enable a reflected light beam 12 to be formed from the incident beam 10. The reflecting means are arranged proximate to the optical path of the second light beam 11, so that the latter reaches the space zone 14, and preferably a sensor 13, directly without being diverted. The reflected beam 12 and the second light beam 11 pass through a zone of the space 14 wherein an object to be analyzed is to be exposed, and they then both reach the same sensor 13. Thus, the optical paths of the reflected beam 12 and of the second beam 11 can possibly cross one another in the zone of the space 14. In the embodiment represented in this figure, the mirror 15 is arranged outside and proximate to the optical path, i.e. in close proximity to the optical path of the second beam but outside the latter. Thus, unlike the separating plate 6 of FIG. 2 and the mirror of the document DE 1,079,857, the second beam 11 does not pass through the mirror 15.

The optical device 6 preferably comprises means for orienting the reflecting means, so as to adjust the optical path of the reflected light beam 12 so that it passes through the zone of the space 14 and reaches the sensor 13. The means for orienting also enable only a part of the optical power of the first incident beam 10 to be transmitted, depending on the reflection coefficient of the reflecting means. The means for orienting can be of any type. For example, they can comprise a hydraulic-based system or screws, actuated by a motor or a pump.

The reflecting means are preferably a mirror or a semi-reflecting plate. They can be formed by a stack of layers of dielectric material thus forming a Bragg mirror or by a metallic deposit, for example made of silver or gold which reflects 97% of the power of a light radiation in the infrared. The reflecting means can also be formed by plates of crystalline materials such as silicon or germanium or plates of vitreous materials such as glass.

The reflecting means preferably comprise support means which can be fixedly secured to the support structure of the optical device or they can be separated from this structure so that they can move with respect to the latter.

Figure 4:
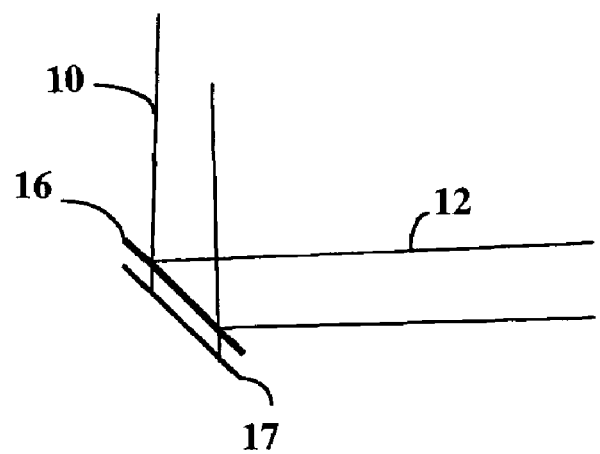
FIGS. 4 and 5 respectively represent first and second embodiments of reflecting means of an optical device according to the invention.

In FIG. 4, the reflecting means are formed by a semi-reflecting plate 16, behind which there is arranged an absorbing element 17 that absorbs at least a part of the first incident beam 10. The light beam 12 reflected by the semi-transparent plate 16 is then attenuated in comparison with the first incident beam 10. This attenuation also depends on the reflection coefficient of the semi-reflecting plate 16. The semi-reflecting plate 16 is preferably arranged on the absorbing element 17, which can be a coating such as a paint or a deposit arranged on the non-reflecting surface of the semi-reflecting plate. The absorbing element 17 can also be formed by an absorbent material on which the semi-reflecting plate is stuck.

Figure 5:
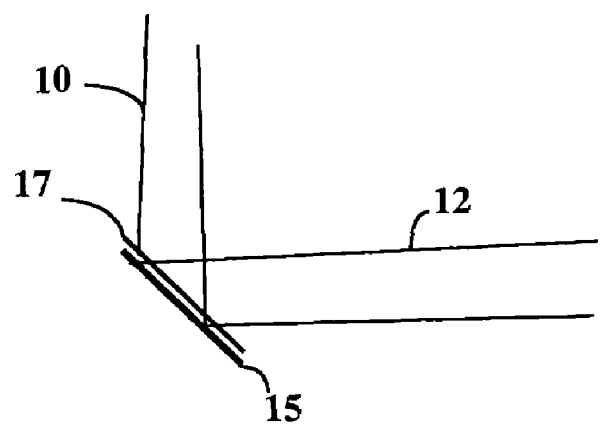

In the case where the reflecting means comprise a mirror 15 (FIG. 5), an absorbing element 17 designed to attenuate the optical power of the first incident beam 10 can also be arranged in front of the mirror 15. The absorbing element 17 is preferably arranged on the reflecting surface of the mirror. It can thus be stuck, deposited or sprayed in the form of a paint aerosol, which enables the absorption of the mirror 15 to be finely controlled.

Figure 6:
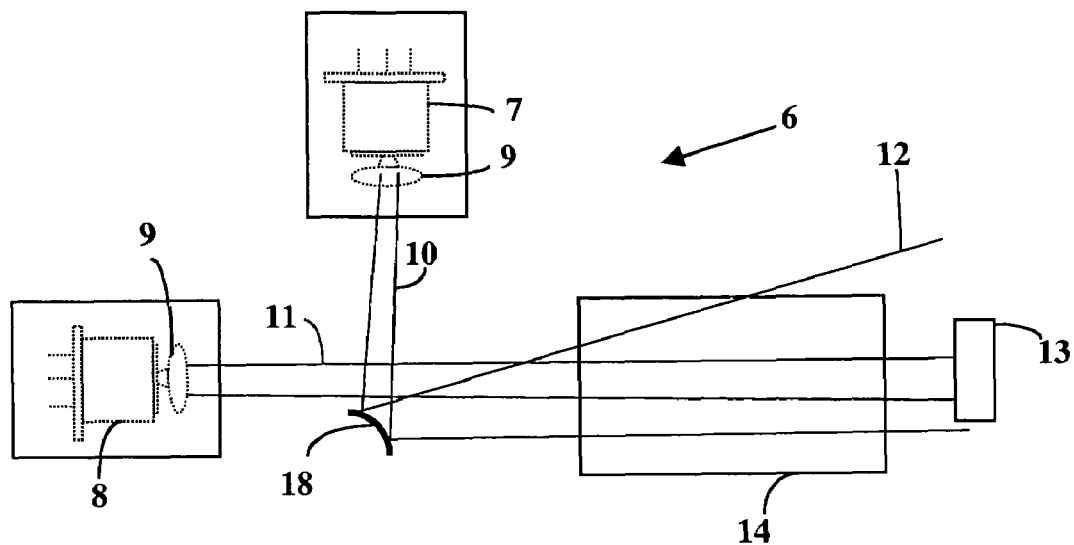
FIGS. 6 and 7 represent second and third embodiments of a device according to the invention.
Figure 7:
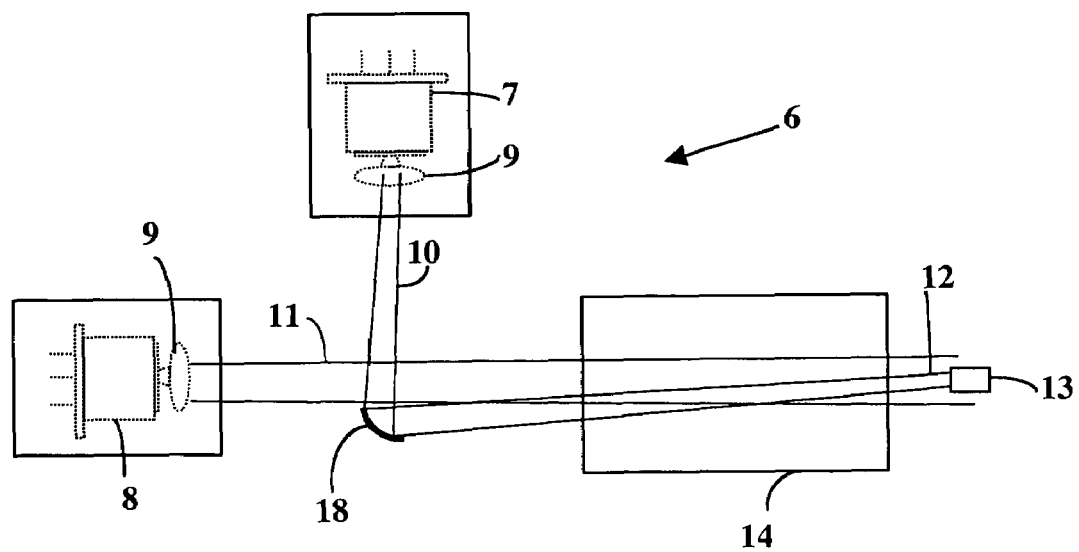

The optical device can also comprise means for deforming the reflecting means. In FIGS. 6 and 7 the reflecting means are formed by a deformable mirror 18. The deformable mirror 18 can for example be formed by a fine metal plate, made of gold or silver, polished on one face. It can also be formed by a reflecting coating deposited on a deformable material, for example a sheet of gold foil stuck onto rubber or onto a metal plate. The deforming means control the curvature of the mirror so as to adjust the optical power received by the sensor precisely.

Thus, a convex mirror 18 (FIG. 6) enables the reflected light beam 12 and in particular the light spot it creates at the level of the sensor 13 to be broadened, whereas a concave mirror (FIG. 7) narrows the reflected light beam 12, in particular the spot created by the reflected beam 12 and detected by the sensor 13. The optical device thus presents the advantage of controlling the power received by the sensor.

The deformation of the mirror is particularly adapted to the power of the first and second sources 7 and 8. Indeed, if the first source 7 is the less powerful of the two sources 7 and 8, the use of a concave mirror 18 (FIG. 7) then enables the reflected beam 12 to be narrowed and focussed more strongly on the sensor 13. If on the contrary the first source 7 is the more powerful of the two sources, the use of a convex mirror 18 (FIG. 6) attenuates the power of the reflected beam 12 by broadening the latter.

Figure 8:
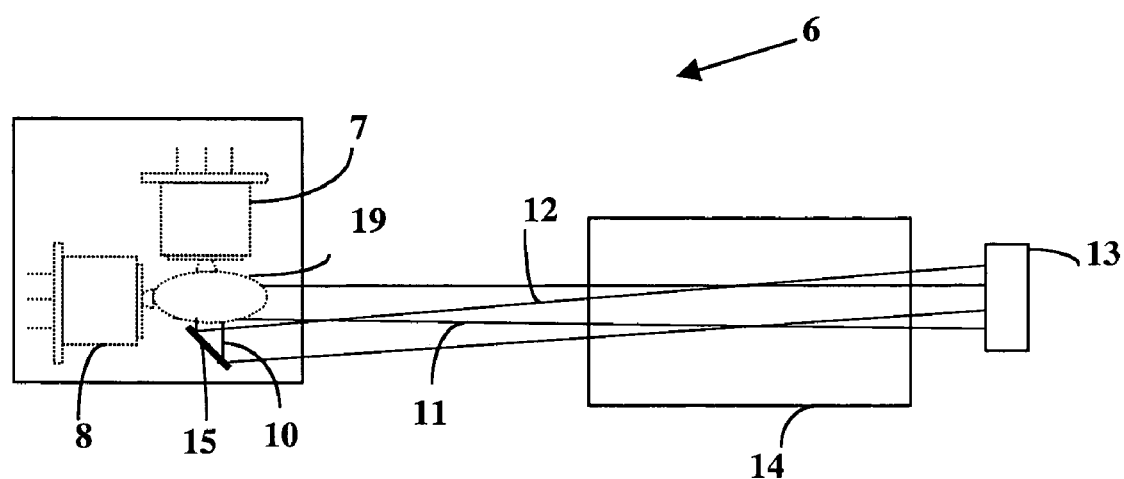
FIGS. 8 and 9 schematically represent an optical device according to the invention, comprising a common collimating lens.
Figure 9:
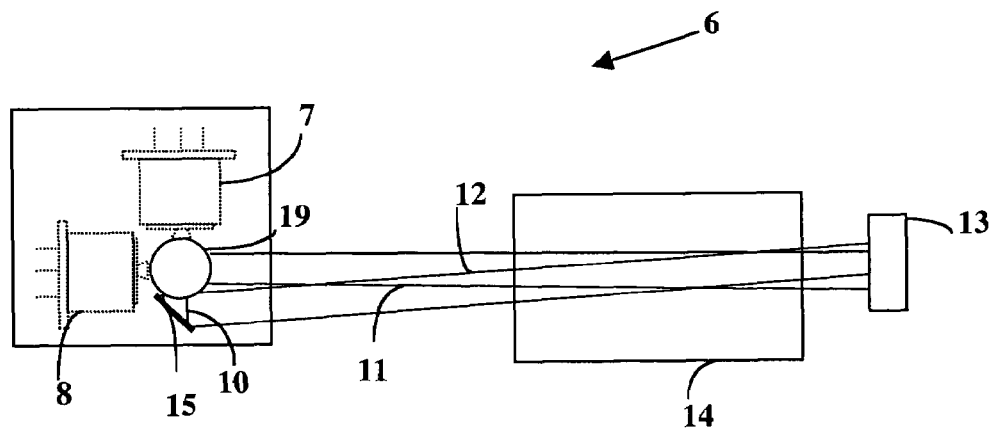

According to an alternative embodiment, the optical device 6 comprises a single collimating lens 19, common to the two optical sources 7 and 8 (FIGS. 8 and 9). The collimating lens 19 is arranged at the intersection of the optical paths of the first incident beam 10 and of the second beam 11. It not only enables the divergence of the two beams to be reduced simultaneously, but also enables focussing of the optical power on the sensor 13, after passing through the zone 14 of the space, to be increased.

Figure 10:
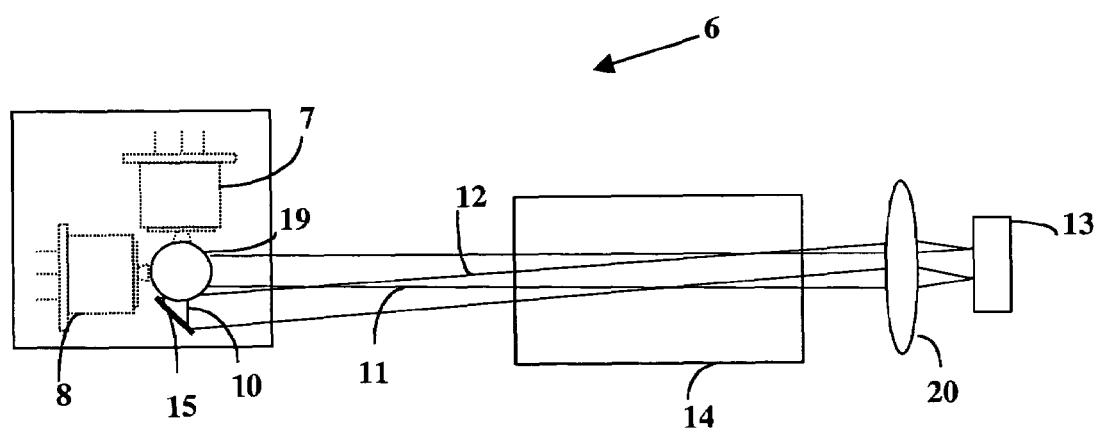
FIG. 10 is a schematic representation of a particular embodiment of a device according to the invention, comprising a lens arranged before a sensor.

In FIG. 9, the collimating lens 19 is perfectly spherical enabling the divergence of the two beams to be reduced simultaneously, overcoming positioning difficulties of the collimating lens 19 with respect to the two optical sources 7 and 8. The optical device can also comprise a lens 20 arranged between the zone of the space 14 wherein the object to be analyzed is to be exposed and the sensor 13 (FIG. 10). The lens 20 enables the reflected beam 12 and the second beam 11 to be focussed on the sensor 13.

For example, the optical device can be used to detect polluting gases, with infrared emitters such as light-emitting diodes or incandescent lamp filaments. Thus one of the beams is designed to be absorbed by the polluting gas and the other acts as reference beam, i.e. it does not absorb any polluting gas but undergoes the same optical disturbances as the first beam. The two beams originating from the optical device pass either through a zone containing the polluting gas or directly to the ambient air, before reaching a single sensor.

The invention is not limited to the embodiments described above. Thus, the sensor can be replaced by an optical fiber. Furthermore, the second beam 11 and the reflected 12 beam may be possibly diverted, after the zone of the space 14, by any type of known means so as to be focussed on the sensor.

The invention claimed is:

1. An Optical device comprising a reflecting element arranged on the optical path of an incident beam emitted by a first optical source so as to form a reflected light beam, and a second optical source producing a second light beam of different wavelength so that the reflected beam and the second light beam pass through a zone of the space wherein an object to be analyzed is to be exposed, and reach a common sensor, wherein the reflecting element is arranged proximate to and outside the optical path of the second beam and wherein the optical device comprises a collimating lens common to the first and second sources and arranged at an intersection of the first incident beam and of the second beam.

2. Optical device according to claim 1, wherein the optical device comprises means for deforming the reflecting means.

3. Optical device according to claim 1, wherein the optical device comprises means for orienting the reflecting means.

4. Optical device according to claim 1, wherein the reflecting means are formed by a mirror.

5. Optical device according to claim 4, wherein an element absorbing a part of a light radiation is arranged on a reflecting surface of the mirror.

6. Optical device according to claim 1, wherein the reflecting means are formed by a semi-reflecting plate.

7. Optical device according to claim 6, wherein the semi-reflecting plate is arranged on an element absorbing a part of a light radiation.

8. Optical device according to claim 1, wherein the collimating lens is spherical.

9. Optical device according to claim 1, wherein a lens is arranged between the zone of the space wherein the object to be analyzed is to be exposed and the sensor.

\* \* \* \* \*